(12) United States Patent
Lundberg et al.

(10) Patent No.: US 7,347,107 B2
(45) Date of Patent: Mar. 25, 2008

(54) DEVICE FOR A TORQUE OR SHEAR FORCE TRANSMITTER FOR THE DETERMINATION OF FIBRE CONCENTRATION OR VISCOSITY IN PULP SUSPENSIONS AND METHOD FOR RESETTING OF THE TRANSMITTER SHAFT IN A TORQUE OR SHEAR FORCE TRANSMITTER

(75) Inventors: Peter Lundberg, Amal (SE); Joakim Kullander, Saffle (SE)

(73) Assignee: BTG Pulp and Paper Sensors AB, Saffle (SE)

( * ) Notice: Subject to any disclaimer, the term of this patent is extended or adjusted under 35 U.S.C. 154(b) by 0 days.

(21) Appl. No.: 10/582,138

(22) PCT Filed: Dec. 6, 2004

(86) PCT No.: PCT/SE2004/001812

§ 371 (c)(1),
(2), (4) Date: Apr. 5, 2007

(87) PCT Pub. No.: WO2005/057153

PCT Pub. Date: Jun. 23, 2005

(65) Prior Publication Data

US 2007/0277595 A1    Dec. 6, 2007

(30) Foreign Application Priority Data

Dec. 9, 2003   (SE) .................................. 0303303

(51) Int. Cl.
*G01L 3/02*   (2006.01)

(52) U.S. Cl. ................................................ 73/862.331
(58) Field of Classification Search ..............................
73/862.331–862.333
See application file for complete search history.

(56) References Cited

U.S. PATENT DOCUMENTS

| | | | |
|---|---|---|---|
| 3,181,349 A | 5/1965 | Jansson | |
| 5,201,214 A | 4/1993 | Sekiguchi et al. | |
| 5,204,619 A * | 4/1993 | Beigbeder et al. | .......... 324/174 |
| 5,987,970 A * | 11/1999 | Ball | ......................... 73/54.28 |
| 6,459,251 B1 | 10/2002 | Enarson | |
| 6,863,913 B1 * | 3/2005 | Navin et al. | ................. 426/231 |

* cited by examiner

*Primary Examiner*—Max Noori
(74) *Attorney, Agent, or Firm*—Young & Thompson

(57) ABSTRACT

Device for a torque or shear transmitter for determining fibre concentration or viscosity in pulp suspensions and which is adapted to measure an angle deviation between two concentric shafts whereby the angle deviation forms a function of the torque applied on the measuring body. The device includes a feedback system for bringing the inner or measuring shaft to a zero position independent of the magnitude of the torque. The system includes an electromagnetic feedback coil, which encircles two pole shoes journalled in bearing points at the end of the outer shaft, at the same time as each pole shoe is connected to the measuring shaft, whereby a current, generated by a transducer and dependent on the angle deviation, is sent to the winding of the coil, where a magnetic field of force is generated.

3 Claims, 4 Drawing Sheets

Section A-A

Figure 1:
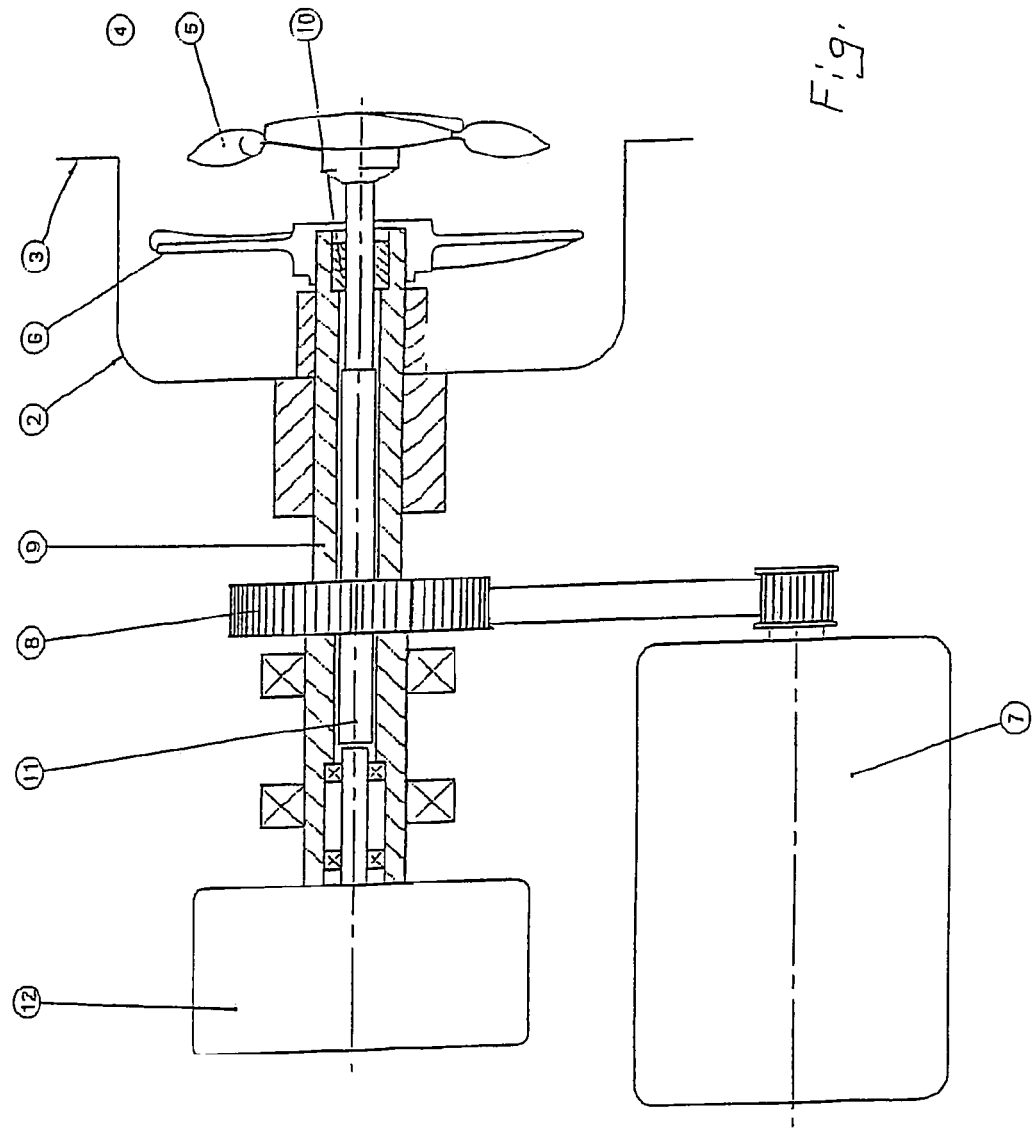

DEVICE FOR A TORQUE OR SHEAR FORCE TRANSMITTER FOR THE DETERMINATION OF FIBRE CONCENTRATION OR VISCOSITY IN PULP SUSPENSIONS AND METHOD FOR RESETTING OF THE TRANSMITTER SHAFT IN A TORQUE OR SHEAR FORCE TRANSMITTER

The present invention concerns a feedback device for torque transmitters, for example for pulp concentration and viscosity, which works according to the force balance principle.

Rotating transmitters for shear forces in pulp suspensions or pure viscosity measurements in other media have been used for a long time within the process industry. The basic principle is based on the fact that a measuring body is forced to rotate in a medium and the arisen torque of resistance on a measuring body or a sensor, as often called, is measured and converted to a suitable output signal, which reflects the present fibre concentration or viscosity.

A commonly present way to effectuate the above mentioned types of measurements is that an angle deviation between two concentric shafts is measured, of which the outer is driven with a constant rotational speed and the inner, which is influenced by the torque of resistance via the measuring body, is elastically connected to the outer one. The angle deviation occurring between the two shafts is a function of the torque on the measuring body. In control engineering matters this is called the motion balance principle. There is, however, obvious drawbacks with such a system, material ageing and/or corrosion, influence of temperature and so on, will influence the characteristics of the system and further that the system, in order to be able to register quick progresses, must have high natural frequency which in turn gives a low sensitivity. The system will also be more or less non-linear. By means of a feedback system bringing the inner shaft to take a zero position irrespective of the size of the arisen torque and to measure the force the feedback system needs to exert on said shaft in order to bring the shaft to take the zero position, the risk of having the above-mentioned drawbacks will drastically decrease. Such a system, which in control engineering matters is said to have feedback and work according to the force balance principle, will become more linear and the response time will be determined by the bandwidth of the system.

Feedback systems are, as can be understood by the text above, not new when it comes to torque measurements and today there are electromagnetic systems, which are relatively complicated and have low efficiency. A complication in the matter is that one is forced to use high quality soft magnetic materials in those parts to be magnetized. These materials are made so that they shall give a minimum of remanence in the magnetization curve of the iron, i.e. the difference in flux system in the same ampere-turn at up and down magnetization, respectively, is as small as possible. The ideal is that the feedback forces the system is to deliver shall only be depending on the ampere-turns. Everything else, for example remanence, is shown in the final stage of the measurement as inaccuracy. Said materials are relatively expensive and difficult to machine and require time consuming heat treatment in brazing atmosphere. Surface treatment is required since the corrosion tendency is pronounced and the availability of the materials in different embodiments and dimensions is low.

One object of the present invention is to minimize the remanence of the system, another is to make it possible to, in the electromechanical circuit, use a commercial and easily machined structural steel with high availability and normal functional tendency. A further object of the invention is to show an accurate, compact system with low weight and high efficiency.

Thanks to the invention, a feedback system for torque transmitters now have been provided, which in an excellent way fulfils its purposes at the same time as the above objects have been met. The pole shoes which are provided on the measuring shaft, which rotate in the field of force of the electromagnet, cause eddy currents which reduce the remanence to a level which is lower than in existing systems, despite the fact that a conventional structural steel is used in those parts that are magnetized. Thus, the production costs can be kept on a lower level than before. The compact design with one feedback coil, instead of conventional two, also contributes to keeping the weight down. The design with double pole shoes gives a statically and dynamically balanced system at the same time as it allows large transfer surfaces on both sides of the gaps between the pole shoes and the steel parts of the electromagnetic coil. The latter contributes to an efficiency, which widely exceeds previous designs and when comparing to an older design it shows that the efficiency has increased with a factor 3.

Figure 2:
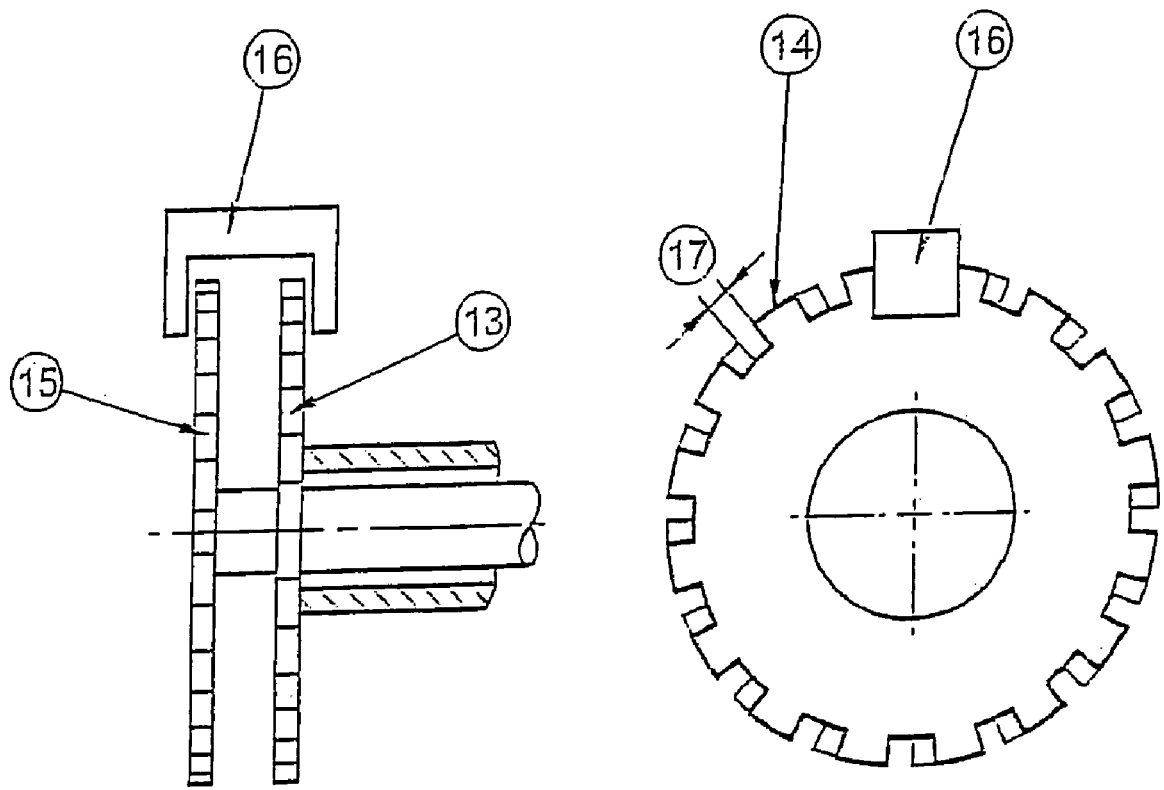
Figure 3:
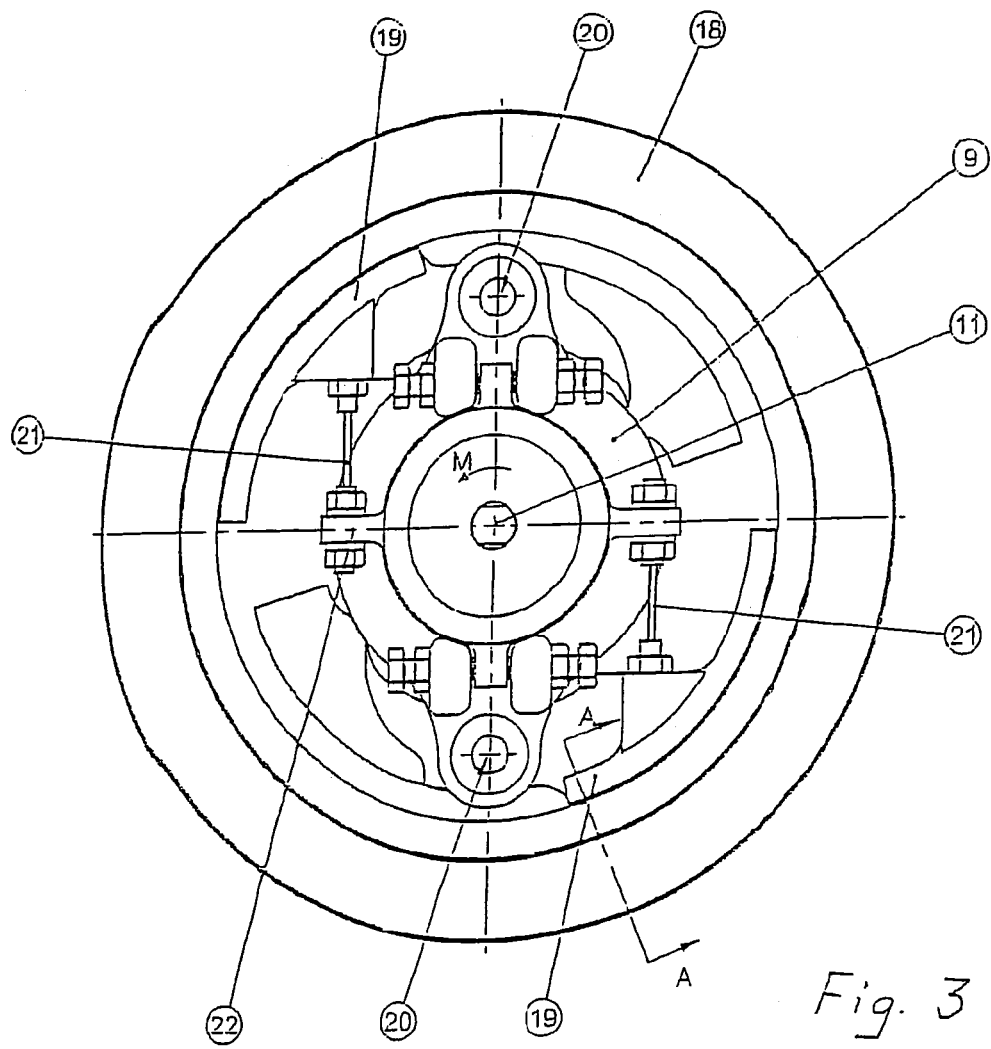
Figure 4:
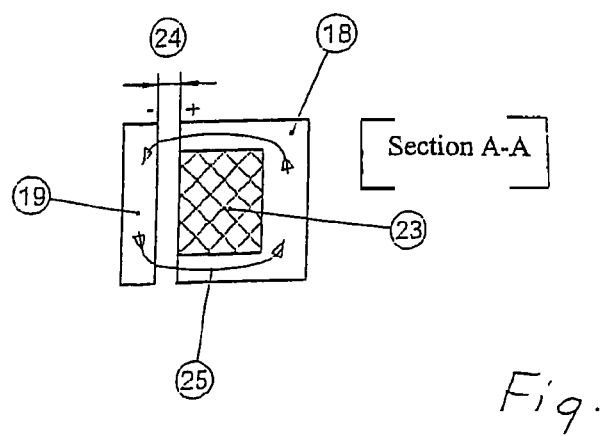
Figure 5:
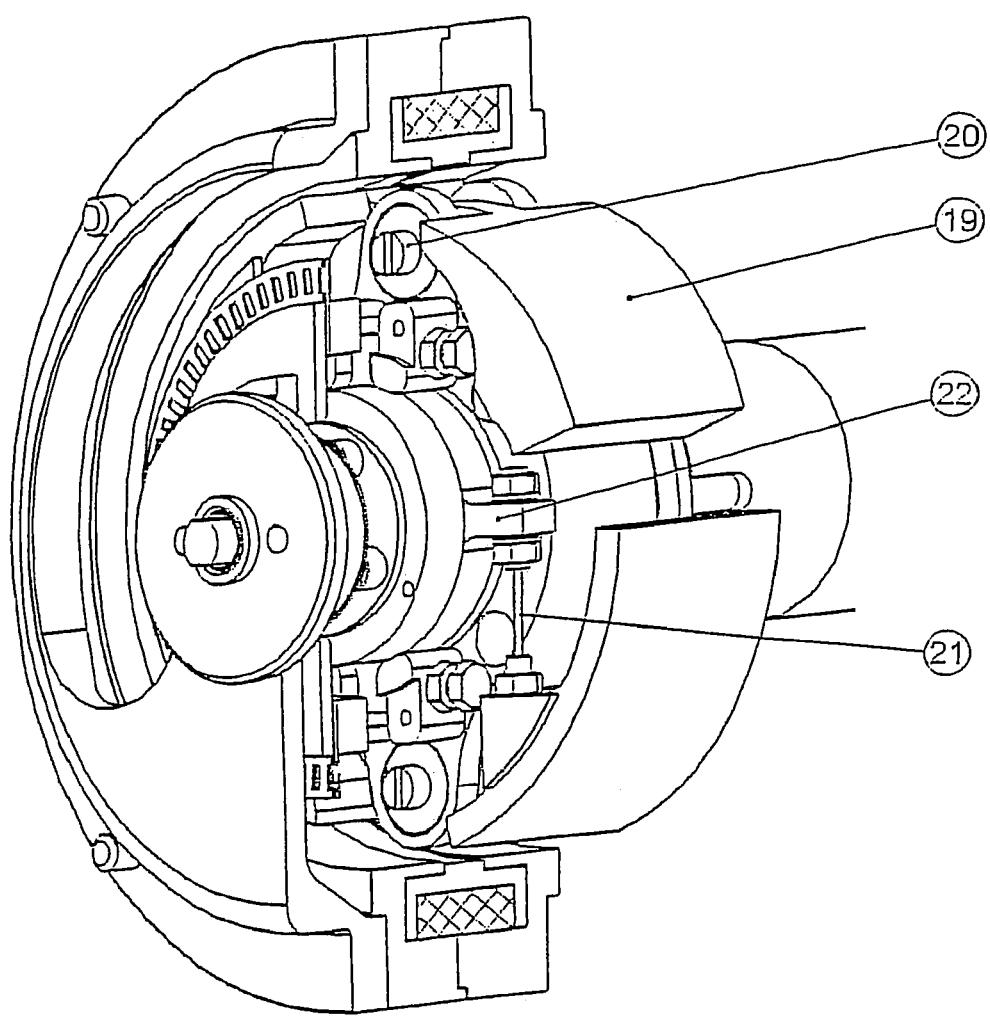

The invention will now be described in more detail below with reference to appended drawings, in which:

FIG. 1 shows a typical structure of a shear force transmitter on which the present invention is applicable, FIG. 2 shows a detector system, FIG. 3 shows a view of an electromagnetic feedback device according to the invention, FIG. 4 shows a cross-sectional view A-A of the magnet circuit as shown in FIG. 3, and FIG. 5 shows a perspective view partly in cross-section, from which the structure of the feedback system emerges.

In FIG. 1 a torque or shear force transmitter is shown, which comprises a connection piece 2, which is weldable to or in another way attachable on a process pipe. In the connection piece 2, where a measuring medium 4 from a process pipe 3 passes by, a measuring body 5 is provided on the transmitter 1 together with a propeller 6, which assures that a representative portion of the measuring media always is present around the measuring body 5. The propeller 6 and the measuring body 5 are driven by a motor 7 via a transmission 8 connected to a hollow shaft 9, in which the propeller 6 and the measuring body 5 are directly and indirectly, respectively, arranged. An elastic connection 10 between the hollow shaft 9 and the measuring shaft 11 allows that both said shafts 9, 11 will obtain a mutual angle deviation upon change of the shear force/torque the media 4 exerts on the measuring body 5. Said angle deviation is detected in a transducer 12 and the feedback force required in order to obtain the same value of the angle signal as a preset set point, is transformed to a suitable signal for the purpose, which signal is fed into the electromagnetic circuit which is present in the feedback system of the invention.

The momentary angle deviation between the hollow shaft 9 and the measuring shaft 11 is detectable in different ways. An alternative and commonly used embodiment is shown in FIG. 2 where a disc 13 with a number of teeth 14 is mounted on the hollow shaft 9 and further a disc 15 with the same number of teeth is mounted on the measuring shaft 11. A detector unit in the form of a light sensor 16, comprising a source of light with a light detector, continuously measures the angle deviation between both said shafts by means of measuring the differences in light opening between the two teeth discs.

As been mentioned above, great advantages are involved in being able to use the force balance principle in torque transmitters and in this way obtain a feedback system. In FIG. 3 an end view is shown and in FIG. 5 a perspective view partly in cross-section of such a device according to the invention. FIG. 4 shows a cross-section through the electromagnetic parts of the feedback system. The system comprises an electromagnetic feedback coil 18, which encircles two pole shoes 19. The pole shoes 19 are journalled in bearing points 20. Each pole shoe has besides the part which is situated closest the electromagnet, on the other side of its bearing point 20 a balance part, whose weight and centre of gravity are adapted so that the centrifugal forces do not influence the system in question. The bearing points 20 are mounted on the end of the hollow shaft 9 and each pole shoe is connected to the measuring shaft 11 via pull rods 21 and a transfer arm 22 mounted on one end of the measuring shaft 11. Through the winding 23 of the electromagnetic coil a current flows, whose strength represents the size of the light opening 17, which in turn represents the angle deviation between the hollow shaft 9 and the measuring shaft 11. This angle deviation is as mentioned above a measurement of the shear force torque the measured medium 4 exerts on the measuring body 5. Besides the fact that the size of the light openings 17 will vary with the size of the shear force torque, also the gap 24 which is present between the magnetic parts of the feedback coil and the magnetic parts of the pole shoes 19 will vary. When a current flows through the coil 23 a magnetic field of force 25 will be formed in the magnetic parts. The strength of the field of force 25 depends on the current that flows through the coil and the distance 24 between the magnetic parts of the pole shoes and the feedback coil. On each side of the gap 24 the magnetic parts will get different polarity and will attract each other. The greater current the greater attraction forces and vice versa. When the torque/shear force increases momentarily the distance 24 will increase at the same time as the light openings 17 change proportionally, the transducer 12 increases the current to the feedback coil 18 and the magnetic field of force 25 increases and pulls the pole shoes 19 back to the preset set point. Since the pole shoes 19 are connected to the measuring shaft 11 via the pull rods 21 and the transfer arm 22, the returning shaft 11 will be fed back to its original position. But the current to the coil is now higher due to the higher shear force torque. The magnitude of the current is a measure of the shear force torque and is converted to an output signal suitable for the purpose.

The invention claimed is:

1. Device for a torque or shear force transmitter for determination of fibre concentration or viscosity in pulp suspensions and which is adapted to measure an angle deviation between two concentric shafts (9, 11), of which the outer is driven with a constant rotational speed while the inner, which is influenced by a present resistance torque in the suspension via a measuring body (5), is elastically connected to the outer, whereby the arisen angle deviation form a function of the torque applied on the measuring body (5), characterized in a feedback system for bringing the inner shaft or measuring shaft (11) to take a zero position independent of the magnitude of the torque, which system comprises an electromagnetic feedback coil (18), which encircles two pole shoes (19) journalled in bearing points (20) at the end of the outer shaft in the form of a hollow shaft (9), at the same time as each pole shoe (19) is connected to the measuring shaft (11), whereby a current, generated by means of a transducer (12) and dependent on the present angle deviation, is sent to the winding (23) of the coil (18), where a magnetic field of force (25) is generated, whose strength is determined by the current flowing through the coil (18) and the distance (24), which arise between the pole shoes (19) and the magnetic parts of the feedback coil, which latter obtain different polarity and provide a resetting of the pole shoes (19) to a preset set point together with the measuring shaft (11) and which current magnitude is a measure of the present shear force torque, which is convertible to suitable output signal.

2. Means according to claim 1, characterized in that each pole shoe (19) is connected to the measuring shaft (11) via pull rods (21) and a transfer arm (22) mounted at the end of the measuring shaft (11).

3. A method for resetting of the measuring shaft in a torque and/or shear force transmitter by means of a feedback system according to claim 1 in order to take zero position independent of the magnitude of the present torque and measure the force the feedback system requires to exert on the measuring shaft in order for it to take zero position, characterized in that the current the transducer (12) sends to the winding (23), of the magnetic feedback coil (18) and which represents the present angle deviation between the hollow shaft (9) and the measuring shaft (11) forms a magnetic field of force (25) in the magnetic parts of the system and which strength of the field of force is determined by the current that flows through the coil (18) and the distance or gap (24) which arises between the magnetic parts of the pole shoes (19) and the feedback coil (18), whereby on each side of the gap (24) the magnetic parts will obtain different polarity and will attract each other and when the torque and/or shear force torque increases momentarily the gap (24) will increase at the same time as the angle deviation between the shafts will change proportionally, the transducer (12) increases the current to the coil (18) and the magnetic field of force (25) increases and pulls the pole shoes (19) back to a preset set point at the same time as the measuring shaft (11) is returned to its initial position.

* * * * *